(12) United States Patent
Dungey

(10) Patent No.: US 9,527,024 B2
(45) Date of Patent: Dec. 27, 2016

(54) SCENT DISPERSING ASSEMBLY

(71) Applicant: Daniel Dungey, Norwich, NY (US)

(72) Inventor: Daniel Dungey, Norwich, NY (US)

( * ) Notice: Subject to any disclaimer, the term of this patent is extended or adjusted under 35 U.S.C. 154(b) by 132 days.

(21) Appl. No.: 14/568,955

(22) Filed: Dec. 12, 2014

(65) Prior Publication Data

US 2016/0166966 A1    Jun. 16, 2016

(51) Int. Cl.
| | | |
|---|---|---|
| B01D 47/00 | (2006.01) | |
| B01F 3/04 | (2006.01) | |
| A61L 9/04 | (2006.01) | |
| B01D 46/00 | (2006.01) | |
| B01D 46/10 | (2006.01) | |

(52) U.S. Cl.
CPC .............. B01D 46/0038 (2013.01); A61L 9/04 (2013.01); B01D 46/0023 (2013.01); B01D 46/10 (2013.01); B01D 47/00 (2013.01); B01F 3/04 (2013.01)

(58) Field of Classification Search
CPC .............. B01F 3/04; B01D 47/00; A61L 9/00; A61L 9/04; A61L 9/015
USPC ...... 261/30, DIG. 88; 422/123, 124; 96/222; 55/503, 511
See application file for complete search history.

(56) References Cited

U.S. PATENT DOCUMENTS

| | | | |
|---|---|---|---|
| 4,604,114 A | 8/1986 | Ward | |
| 5,415,675 A | 5/1995 | Powers et al. | |
| 5,547,636 A * | 8/1996 | Vick | A61L 9/042 239/60 |
| 5,817,168 A | 10/1998 | Wheless | |
| 6,117,218 A * | 9/2000 | Snyder | A61L 9/048 261/DIG. 17 |
| 8,182,568 B2 | 5/2012 | Volo et al. | |
| D679,792 S | 4/2013 | Hollingsworth | |
| 2012/0234175 A1 | 9/2012 | Sanchez | |

FOREIGN PATENT DOCUMENTS

| | | | | |
|---|---|---|---|---|
| JP | 2000126528 A | * | 5/2000 | ............ B01D 46/00 |
| WO | WO2004073823 | | 9/2004 | |

* cited by examiner

Primary Examiner — Robert A Hopkins

(57) ABSTRACT

A scent dispersing assembly includes a frame coupled to an air handler. A filter is coupled to the frame to filter particles from air urged by the air handler. A second frame is coupled to the air handler such that the second frame is aligned with the frame. A second filter is coupled to the second frame to filter particles from air urged by the air handler. A pad is positioned between the filter and the second filter. The pad is infused with a scent, releasing the scent into the air urged by the air handler.

5 Claims, 4 Drawing Sheets

SCENT DISPERSING ASSEMBLY

BACKGROUND OF THE DISCLOSURE

Field of the Disclosure

The disclosure relates to scent devices and more particularly pertains to a new scent device for releasing a scent from a furnace filter.

SUMMARY OF THE DISCLOSURE

An embodiment of the disclosure meets the needs presented above by generally comprising a frame coupled to an air handler. A filter is coupled to the frame to filter particles from air urged by the air handler. A second frame is coupled to the air handler such that the second frame is aligned with the frame. A second filter is coupled to the second frame to filter particles from air urged by the air handler. A pad is positioned between the filter and the second filter. The pad is infused with a scent, releasing the scent into the air urged by the air handler.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
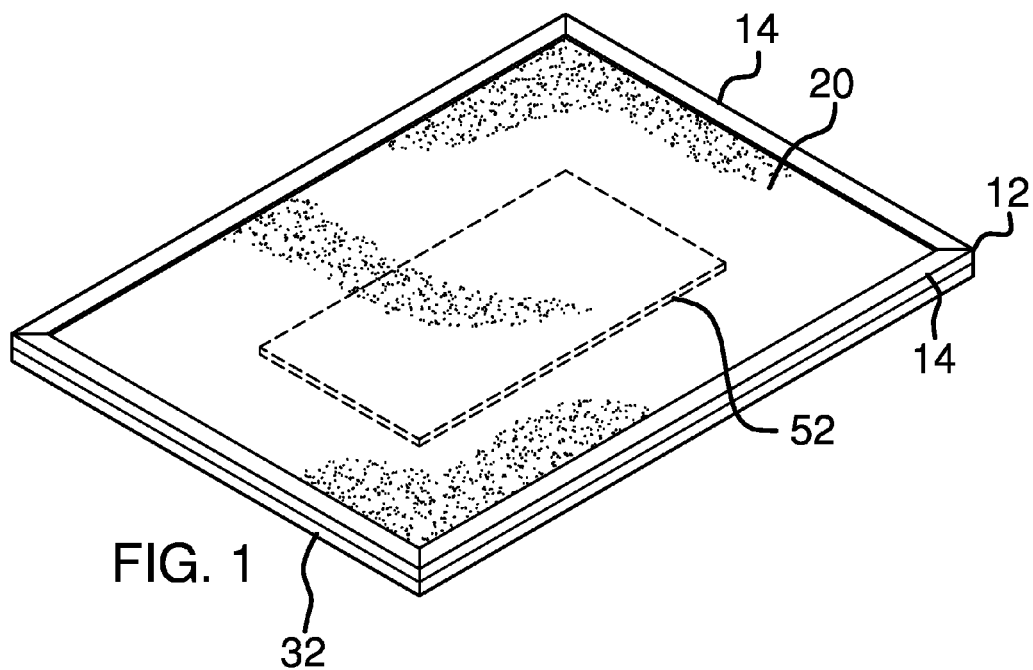
FIG. 1 is a top perspective view of a scent dispersing assembly according to an embodiment of the disclosure.
Figure 2:
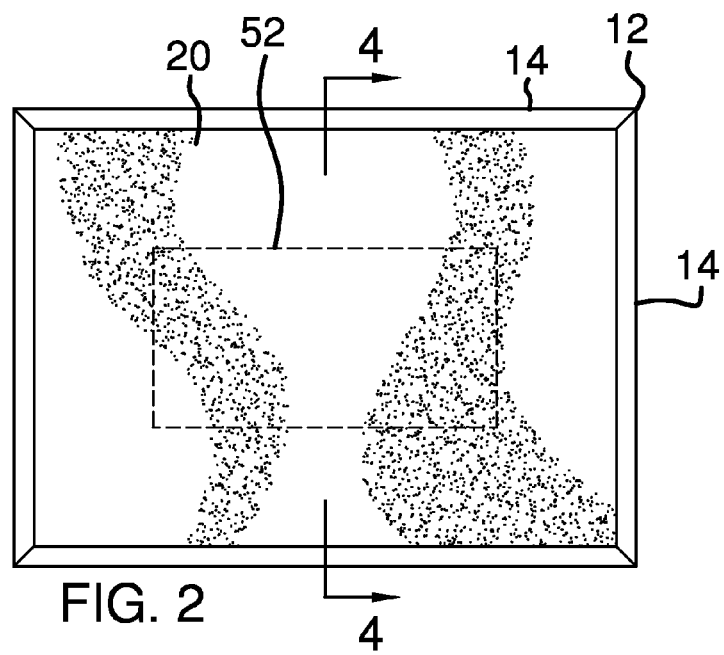
FIG. 2 is a top view of an embodiment of the disclosure.
Figure 3:
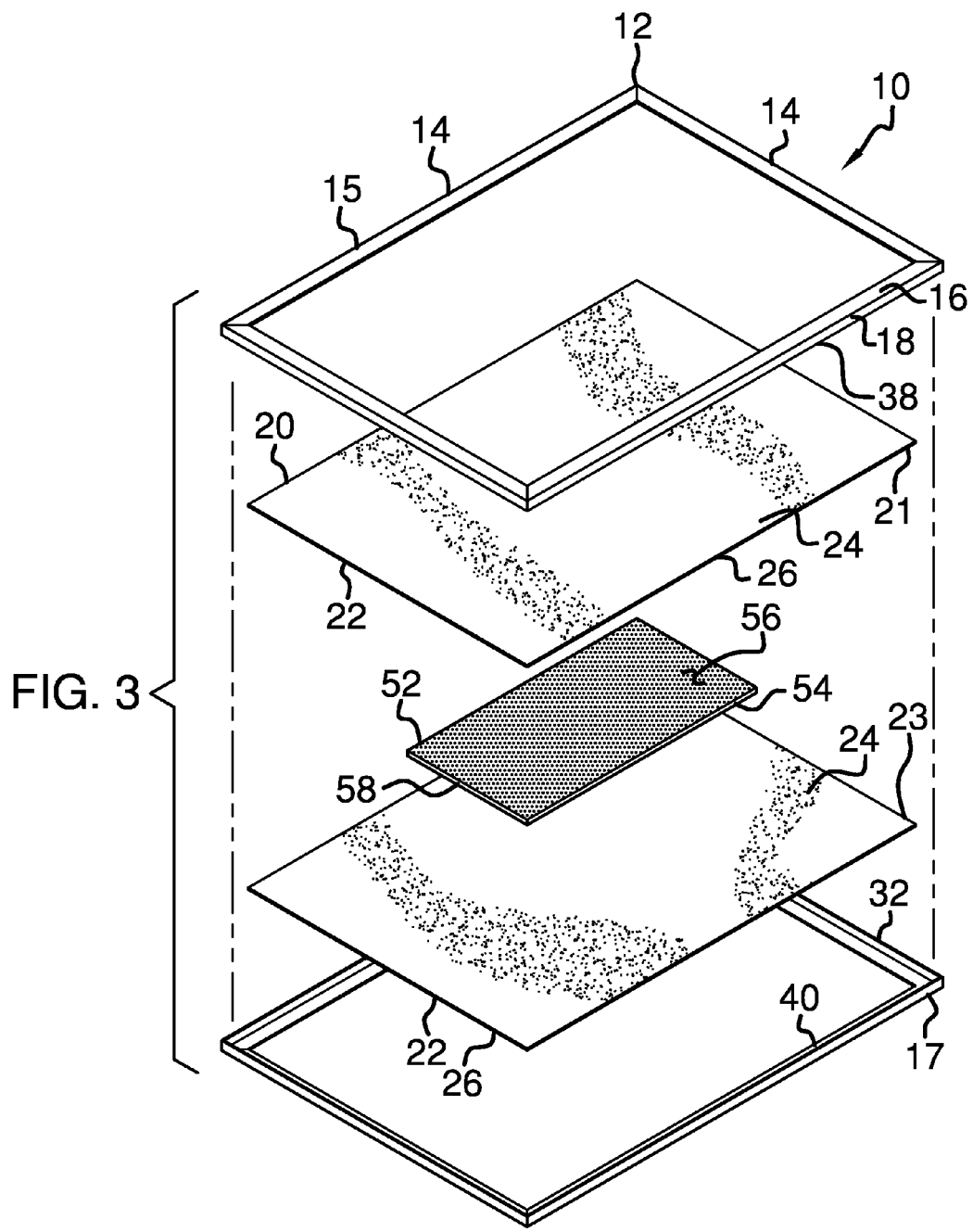
FIG. 3 is an exploded perspective view of an embodiment of the disclosure.
Figure 4:
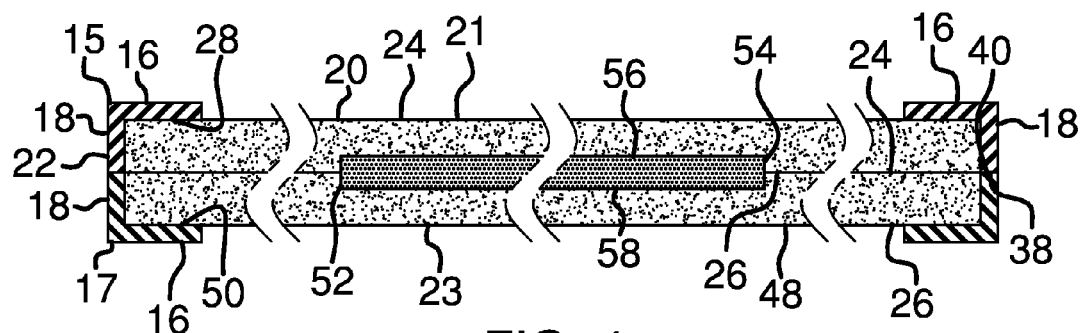
FIG. 4 is a cross sectional view taken along line 4-4 of FIG. 2 of an embodiment of the disclosure.

With reference now to the drawings, and in particular to FIGS. 1 through 6 thereof, a new scent device embodying the principles and concepts of an embodiment of the disclosure and generally designated by the reference numeral 10 will be described.

As best illustrated in FIGS. 1 through 6, the scent dispersing assembly 10 generally comprises a frame 12 coupled to an air handler 13. The air handler 13 may be an HVAC system or the like. The frame 12 is longitudinally split to define an upper half 15 and a lower half 17. Each of the upper half 15 and the lower half 17 comprise a plurality of arms 14. Each of the arms 14 intersects to form an open rectangular shape. Moreover, each of the arms 14 is bent along a lengthwise axis to define a respective first section 16 that forms a right angle with a respective second section 18. Each of the upper half 15 and the lower half 17 are aligned with each other such that a bottom edge 38 of each of the first sections 16 abuts a top edge 40 of an associated one of the primary sections 34.

A filter 20 is provided. The filter is longitudinally split to define a top half 21 and a bottom half 23. Each of the top half 21 and the bottom half 23 has an outer edge 22 extending between each of a top side 24 and a bottom side 26 of the filter 20. The top half 21 is positioned such that the top side 24 abuts a bottom surface 28 of the first section 16 of each of the arms 14 of the upper half 15. Moreover, the filter 20 is coextensive with the frame 12 to filter particles from air urged by the air handler 13. The filter 20 may be HEPA filter or the like. The bottom half 23 is positioned such that the lower side 48 abuts a topmost surface 50 of the first section 16 of each of the arms 14 of the bottom half 23. Additionally, the bottom half 23 is coextensive with the bottom half 23 to filter particles from air urged by the air handler 13.

A pad 52 is provided. The pad 52 has an outermost edge 54 extending between each of an uppermost surface 56 and a lowermost surface 58. The pad 52 is positioned such that the uppermost surface 56 abuts the bottom side 26 of the top half 21 and the lowermost surface 58 abuts the upper side 46 of the bottom half 23. The pad 52 has a length and a width that is less than a length and a width of the filter 20. The pad 52 is centrally positioned on the filter.

Figure 5:
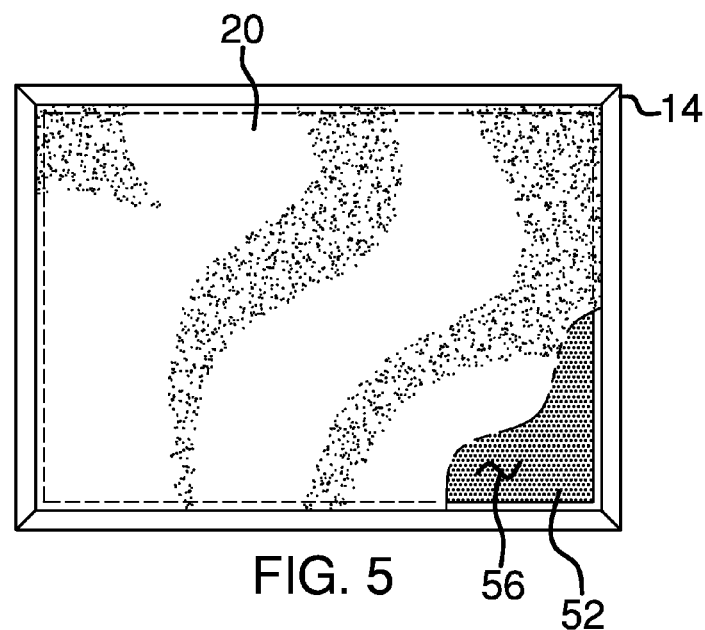
FIG. 5 is a top view of an alternative embodiment of the disclosure.
Figure 6:
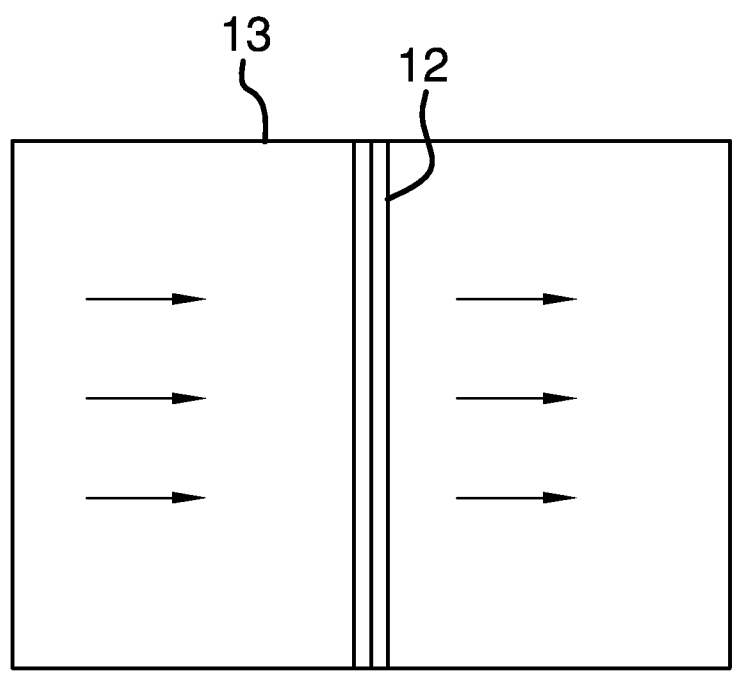
FIG. 6 is an in-use view of an embodiment of the disclosure.

The pad 52 may be comprised of a fabric. The pad 52 may further be comprised of a gel material embedded into the fabric. The pad 52 is infused with a scent 54, thereby releasing the scent 54 into the air urged by the air handler 13. The scent 54 may be a liquid scent or the like. Additionally, the scent 54 may come in a variety of fragrances. In an alternative embodiment as shown in FIG. 5, the pad 52 may have a length and a width that is similar to the length and width of each of the filter 20 and the second filter 42.

In use, the assembly 10 is used to disperse a pleasing scent 54 from the air handler 13. The filter 20 provides an extended service life compared to a single element filter. Additionally, the scent 54 may be chosen according to a desired fragrance.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A scent dispersing assembly comprising:
   a frame configured to be coupled to an air handler;
   a filter coupled to said frame wherein said filter is configured to filter particles from air urged by the air handler;
   a pad coupled to said filter, said pad being infused with a scent wherein said pad is configured to release said scent into the air urged by the air handler;
   said frame being longitudinally split to define an upper half and a lower half, each of said upper half and said lower half comprising
      a respective plurality of arms, each of said arms intersecting to form an open rectangular shape, each of said arms being bent along a lengthwise axis to define a respective first section forming a right angle with a respective second section, and
   each of said upper half and said lower half being aligned such that a bottom edge of each of said first sections abuts a top edge of an associated one of said primary sections; and
   wherein said filter being longitudinally split to define a top half and a bottom half, each of said top half and said bottom half having a respective outer edge extending between each of a respective top side and a respective bottom side.

2. The assembly according to claim 1, wherein said top half of said filter being positioned such that said top side abuts a bottom surface of said first section of each of said arms of said upper half of said frame wherein said top half is coextensive with said upper half.

3. The assembly according to claim 2, wherein said bottom half of said filter being positioned such that said lower side abuts a topmost surface of said first section of each of said arms said lower half of said frame wherein said bottom half is coextensive with said lower half.

4. The assembly according to claim 3, wherein said pad having an outermost edge extending between each of an uppermost surface and a lowermost surface, said pad being positioned such that said uppermost surface abuts said bottom side of said top half and said lowermost surface abuts said upper side of said bottom half.

5. A scent dispersing assembly comprising:
   a frame configured to be coupled to an air handler, said frame being longitudinally split to define an upper half and a lower half, each of said upper half and said lower half comprising
      a respective plurality of arms, each of said arms intersecting to form an open rectangular shape, each of said arms being bent along a lengthwise axis to define a respective first section forming a right angle with a respective second section, and
      each of said upper half and said lower half being aligned such that a bottom edge of each of said first sections abuts a top edge of an associated one of said primary sections;
   a filter coupled to said frame wherein said filter is configured to filter particles from air urged by the air handler, said filter being longitudinally split to define a top half and a bottom half, each of said top half and said bottom half having a respective outer edge extending between each of a respective top side and a respective bottom side;
   said top half of said filter being positioned such that said top side abuts a bottom surface of said first section of each of said arms of said upper half of said frame wherein said top half is coextensive with said upper half;
   said bottom half of said filter being positioned such that said lower side abuts a topmost surface of said first section of each of said arms said lower half of said frame wherein said bottom half is coextensive with said lower half; and
   a pad, said pad having an outermost edge extending between each of an uppermost surface and a lowermost surface, said pad being positioned such that said uppermost surface abuts said bottom side of said top half and said lowermost surface abuts said upper side of said bottom half, said pad being infused with a scent wherein said pad is configured to release said scent into the air urged by the air handler.

* * * * *